United States Patent [19]

Jokl

[11] 4,006,350
[45] Feb. 1, 1977

[54] METHOD FOR PERFORMING A SEPARATING ANALYSIS

[75] Inventor: Jan Jokl, Prague, Czechoslovakia

[73] Assignee: Ceskoslovenska akademie ved, Prague, Czechoslovakia

[22] Filed: Apr. 3, 1975

[21] Appl. No.: 564,675

[30] Foreign Application Priority Data

Apr. 4, 1974 Czechoslovakia ............... 2422/74

[52] U.S. Cl. .................. 235/151.35; 23/230 R
[51] Int. Cl.² ................................ B01D 15/08
[58] Field of Search ........... 235/151.35; 23/230 R, 23/253 R; 73/53, 23.1

[56] References Cited

UNITED STATES PATENTS

| | | | |
|---|---|---|---|
| 3,119,995 | 1/1964 | Burk et al. .................... | 340/347 |
| 3,562,501 | 2/1971 | Mears .......................... | 235/151.35 |
| 3,633,404 | 1/1972 | Chandler ..................... | 235/151.35 X |
| 3,826,905 | 7/1974 | Valkama et al. ............ | 235/151.35 X |

*Primary Examiner*—Edward J. Wise

[57] ABSTRACT

A separating analysis, particularly a continuous quick chromatographic analysis is performed by introduction of doses of the sample to be analyzed into a separating column at pseudorandom sequences and by detecting concentrations of components of the sample at the output of the separating device at a rhytmus of the dosing orders and evaluating the separating analysis by summarizing the read values.

11 Claims, 4 Drawing Figures

METHOD FOR PERFORMING A SEPARATING ANALYSIS

BACKGROUND OF THE INVENTION

The invention relates to a method for performing a separating analysis, particularly a quick continuous liquid chromatographic analysis, where the sample is dosed into a separating device and signals corresponding to the concentration of the individual components of the sample are detected by a sensor within certain time intervals. The invention also relates to an arrangement for execution of this method.

Separating analysis are rather unsuitable if components of analyzed mixtures have to be separated and determined continuously and/or within a wide range of mutual concentration ratios and are ineffective, if the overall concentration of the sample is as to its order equal or even lower than the sensitivity of the sensor. As example of a similar analysis there can be mentioned the modern method of liquid chromatography.

Classical methods of liquid chromatography have not found more extensive application, compared to other analytical methods. Only the introduction of sensitive detectors, of modern filter columns and particularly the introduction in use of pressures up to hundreds of atmospheres have brought a number of important advantages resulting in the creation of an entirely new instrumental manufacturing branch of continuous quick pressure liquid chromatography devices. A number of manufacturers have started manufacture of special arrangements and the method is more and more widely applied. This method has however in addition to its advantages also a number of drawbacks. The high pressures require the use of pumps, delivering a constant not pulsating pressure. The design of similar pumps and pressure shock absorbers is not easy; it is expensive and residual pressure variations increase the noise of all known detectors. There are problems furthermore due to the influence of temperatures and occasional troubles due to variations of the resistance which the columns offer to the throughflowing medium. Finally, the discontinuity of the analysis does not permit in a simple manner the creation of continuous processes. An important drawback lies also in the circumstance, that the sensors do not ideally have linear characteristics and are not sensitive within a wide range of concentrations. Further, while the sensors determine well either major or minor components of the analyzed mixture, they never determine with accuracy both simultaneously, but only inaccurately determine the concentration ratio of these components. Also the influence of other kinds of noise for instance of a thermal noise in addition to the required signal reduces the accuracy and sensitivity of the analysis and cannot be eliminated with a large number of repeated analysis.

A method for continuous separating analysis is described in the British patent specification No. 1,036,624 in which an example of a quick continuous liquid chromatographic analysis is described. According to this method the sample is dosed repeatedly in a concentration which is periodically varied with the same number of frequences as analyzed components are supposed to exist. A further supposition is a variable flow speed of the liquid. A synchronous detection is used for each component and therefore also for each frequency, and a mathematical analysis of the proposed method is also provided. The arrangement for execution of this method is practically so complicated and therefore also expensive, that the operation of the arrangement is in practice limited to several analyzed components only and the accuracy of the results is reduced. It is probably for these reasons that this solution has not been applied in practice according to available sources.

SUMMARY OF THE INVENTION

It is an object of this invention to provide a solution for a method of a separating analysis, preferably a quick continuous liquid chromatographic analysis, where the sample is dosed into the separating device and a signal is detected on the output side of the separating device, corresponding to the concentration of individual components of the sample within a given time interval. In the method the sample is dosed in pseudorandom sequences according to a program, containing a suitable number of orders, advantageously $2^n - 1$ orders, where n is an integer positive number, whereby the orders are preferably of a binary character, repeated advantageously at a regular rhytmus and the instantaneous values of the output signal, proportional to the instantaneous summary concentrations of the components of the sample, are read in a rhytmus which is proportional, preferably equal to the rhytmus of the dosing orders, whereafter the evaluation of the separating analysis is made, carried out in a controlled manner by using the program for dosing of the sample, by summation of the read values. In the course of an analysis of one type, equal doses of the sample are preferably used in pseudorandom sequences. The amount of the sample in one dose is proportional to the sensitivity of the sensor within its range of its linear response. The suitable number $x$ of orders, advantageously $2^n - 1$ where $n$ is an integer positive number, corresponds to the required fineness of separation for instance of the chromatographic separation. The rhytmus of orders for dosing the sample and for reading the instantaneous values of the output signal can be varied in order to obtain a compensation for changes of separation properties of the separating device. The time of duration of one pseudorandom sequence, determined by the rhytmus and number of orders advantageously $2^n - 1$, is equal or longer than the time interval of passage of the slowest component through the separating device, for instance through the chromatographic column. In order to obtain complete information about all separable components of the sample, the number of read values is equal to the number of orders of one pseudorandom sequence according to the program, preferably $2^n - 1$. In case of a real analysis, where a limited number of components is followed, the number of sums is equal to the sum of the number of selected components of the sample and to the selected number of reference sums. The result of the first summation is selected as the main reference sum, as it corresponds to a component with infinite speed, i.e. to non-real component. The control of the end of the separating process, the result of the $x^{th}$, i.e. of the last summation is selected as reference and check sum.

When evaluating the separating analysis, the values of the output signal of the detector, proportional to the sum of instantaneous concentrations of components of the sample, recorded at a rhytmus proportional, preferably equal to the rhytmus of dosing orders on the first summation are added, or not added according to the instantaneous inary state of the fundamental pseudorandom sequence $x$ of the binary elements, whose number is $x$, contained in the program, whereby for the second, third, fourth up to $x^{th}$ summation the values of the output signal are added or not added according to the instantaneous binary state of the pseudorandom sequence, which is derived from the fundamental pseudorandom sequence contained in the program for dosing by cyclic shift by one, two, three up to $(x-1)$ position. The result of the first summation is proportional to the overall content of all components of the sample and it is therefore reasonable to use it as an internal standard of the analysis. The signal of the detector is advantageously recorded and the record is compared with the model record. The results of the second to $x^{th}$ summation are proportional to the overall content of all components of the sample and to the content of the second to the $x^{th}$ component of the sample, whereby the sequence of the components 2 to $x$ is proportional to the speed of passage of individual components through the separating device. When checking automatically the whole separating process according to this invention, the result of the first summation is digitally compared with results of the second to $x^{th}$ summation.

The arrangement for execution of the method according to this invention consists of a separating column, to the inlet of which a dosing device for dosing the sample is attached and to its outlet a detector is connected, whereby the inlet of the dosing device is joined with the output of the source of pseudorandom sequences of orders. The output of the detector is thereby joint with the input of an amplifier, the output of which is connected with the input of an analog-digital converter. The output of this converter is connected to inputs of gates, the control inputs of which are connected with second outputs of the source of pseudorandom sequences of orders and the outputs of these gates are connected separately with inputs of counters. The input of an analog recorder can be advantageously connected to the output of the amplifier. A multichannel digital recorder can be advantageously connected to the output of the analog-digital converter. The source of pseudorandom sequences is composed of a rotor of non-transparent material provided with openings and of a stator with photoelectric indicators for the rotor openings, whereby the photoelectric indicators are arranged so as to enable their relative displacement.

The advantages of the method and arrangement according to this invention can be summarized as follows:

1. The problem of continuous chromatography (in general the separating process) becomes practically feasible;

2. No internal standards for calibrating are required, the concentration of individual components can be directly related to the total concentration of all components, which is by the novel method provided automatically and also continously;

3. The correct function of the whole chain of instruments can be continuously checked by comparison of individual results and their independently determined sum;

4. The flexibility of the new method is such that the number of elements (particularly of counters) can be varied according to the required number of determined components of the sample, the required fineness of the result can be easily adjusted by the number of recording elements of the programming device;

5. Highly diluted solutions or suspensions of samples, which cannot be measured by application of known methods can still be measured with the new method due to the increased sensitivity. The proposed method has been theoretically verified in detail on a mathematical model using a calculator Wang 614 with newly proposed programs and also experimentally on a gel liquid chromatograph of Watters A.S. model AIC 100, where at the maximum sensitivity of the instrument, according to the catalogue amounted to $3.10^{-8}$ units of the index for refraction of light, and therefore at the maximum noise a polymer sample could be still measured, it has been measured by application of the new method without any adjustments of the device, merely by repeating many times the manual introduction of the sample for analyzing, strictly according to instructions of the manufacturer and at intervals according to the new method. The integral chromatogram thus obtained has been again manually evaluated according to the new method. A completely satisfactory chromatogram has been obtained. Thus the advantages of the invention have been checked theoretically and practically. In the given case the sensitivity has been vertically increased to $3.10^{-10}$ units (i.e. 100 times) of the index for refraction of light;

6. The new method brings about a substantially better ratio of signal to noise;

7. The dynamics of the new method, that is the ratio of high and low concentrations of the components of the sample which still correctly reproduced are according to the used type of detector better by several orders of magnitude, than in known types of chromatographs, as the detector of concentration can operate within the range of its optimum linear part of the characteristic;

8. The new method enables the application of detectors, which up to now could not be used due to their limited linear range of their characteristic;

9. If an extreme reliability of measurements is required, the new method enables to utilize the same programming block for control of several, simultaneously working (for instance 3) independent separating devices (chromatographic columns);

10. If the detector signal is recorded by an analog recorder, it is possible to obtain additionally (in case of failures or the like) a complete picture of all separated components of the sample, i.e. not only of those which are followed by the programmed method. (A simple evaluating diagram has been worked out for this case).

11. The new method can be applied also for a single, non-continuous analysis, where the dosing lasts one working period T only, whereby all remaining advantages besides the continuity are maintained;

12. It is possible to compensate objectively and automatically for changes in separating a chromatographic column by proportional change of the relative position of the detectors of properties or by a change of the working rhytmus of the whole arrangement; thus the time of use of the filling of the columns is prolonged;

13. The chromatographic column operates at steady equilibrium conditions. A consequence thereof is a better separation of the components and a reduction of the mutual influence of individual components;

14. The new method is suitable for automation and control particularly of chemical and biological processes due to its continuous character and digital output;

15. It can be applied also to existing separating devices such as gas, liquid-gas, liquid chromatographs, devices for electrophoresis, devices for countercurrent distributing and the like.

16. For a qualitative following of continuous processes it is possible to use in an economical version of the apparatus only the analog record of the summed signal of the detectors - without treatment in the evaluation block with the possibility of a quantitative evaluation with the same program as in point 10.

DESCRIPTION OF THE DRAWINGS

The invention will be in the following described in detail on hand of drawings, where.

DESCRIPTION OF PREFERRED EMBODIMENT

Figure 1:
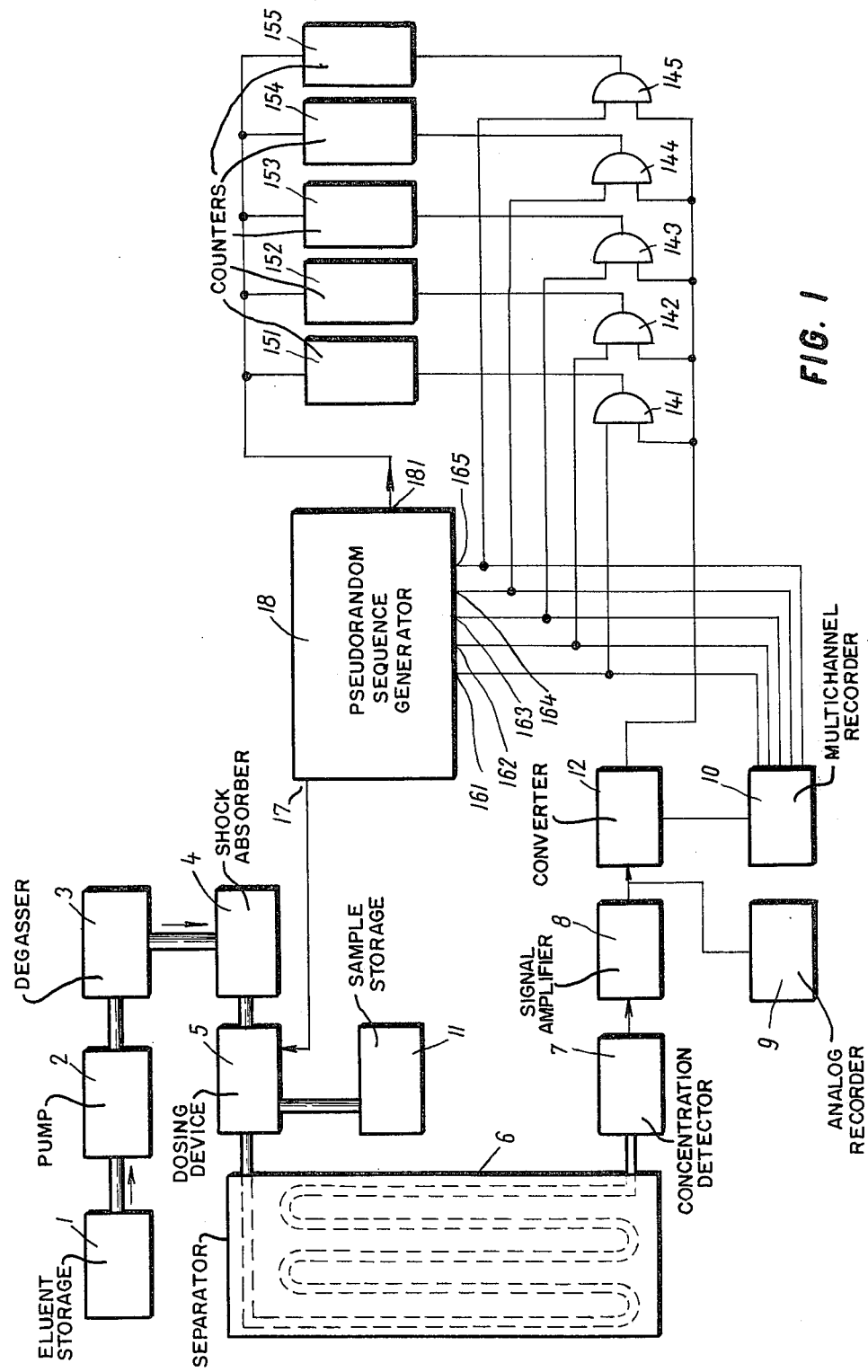
FIG. 1 is a block diagram of the arrangement according to this invention.

The storage tank 1 of the liquid eluent (FIG. 1) is connected to the suction inlet of a pump 2. The pressure outlet of the pump 2 is connected to a degasifier 3 of the eluent. This degaser 3 is connected to a pressure shock absorber 4. The shock absorber 4 is furthermore connected to a dosing device 5, so that the liquid eluent is fed thereto. A second storage vessel 11 for the sample to be analyzed is connected to the inlet of the dosing device. The output of the dosing device 5 for the combined mixture of the liquid eluent and of the sample to be analyzed is connected to the inlet of the separating device 6, in this case to the inlet of a column for pressure liquid chromatography. The outlet from the separating device 6 is connected to a detector 7 of the concentration. The output of the voltage signal of the concentration detector 7 is interconnected with the signal amplifier 8. The output of this amplifier is connected to the input of the analog recorder 9 and to the input of the analog-digital converter 12.

The output of the analog-digital converter 12 is connected to inputs of gates 141, 142, 143, 144, 145. The outputs of the gates 141, 142, 143, 144, 145 are respectively connected to inputs of individual counters 151, 152, 153, 154, 155. The control inputs of the gates 141, 142, 143, 144, 145 are connected with the second outputs 161, 162, 163, 164, 165 of the source 18 of pseudorandom sequences, the first output 17 thereof is connected to the control input of the dosing device 5. the third output 181 of the source 18 of pseudorandom sequences is connected to the clock inputs of counters 151, 152, 153, 154, 155.

Figure 2:
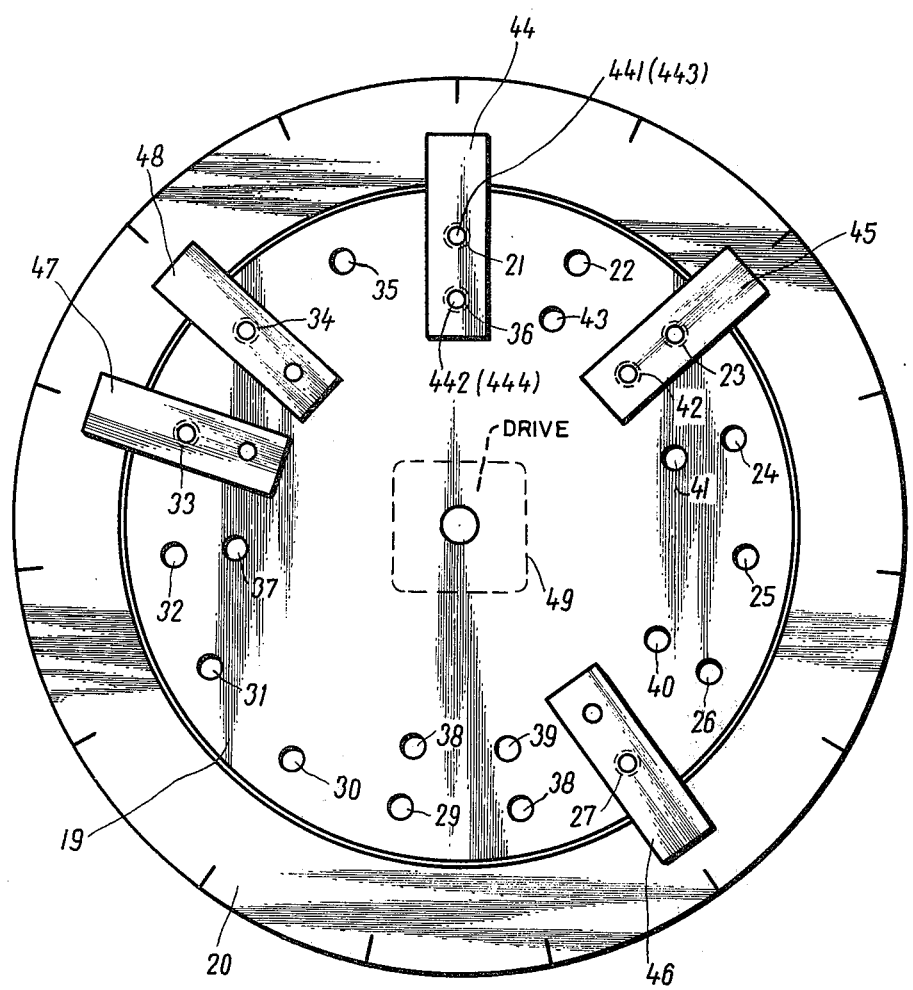
FIG. 2 is a block diagram of a source of pseudorandom sequences of orders with an example of an optical-mechanical reading of the recorded program.

FIG. 2 shows an examplary embodiment of a pseudorandom sequence generator 18 of pseudorandom sequences. The source 18 as indicated comprises a rotor 19 represented by a circular plate of light impervious material, having two rows of openings near its circumference, one of which rows (namely openings 21 - 35) is distributed uniformly. The number of these openings is equal to the chosen number x of orders, in the given case 15 openings. The second row of openings 36, 37, 38, 39, 40, 41, 42 and 43 is arranged with respect to the first row according to a pseudorandom sequence of orders, namely 1, 0, 0, 0, 1, 0, 0, 1, 1, 0, 1, 0, 1, 1, 1, - the occurence of openings of the second row corresponding to condition 1 of the sequence. The rotor 19 is provided with a driving device 49. Photoelectric indicators 44, 45, 46, 47 and 48 corresponding to the openings of both rows of the rotor 19 are arranged on a stator 20. These indicators 44, 45, 46, 47, 48 are adjustably mounted on the stator 20 so that they can be transversed. On the indicator 44 there are photoemissive diodes 441, 442 and phototransistors 443, 446 indicated.

Figure 3:
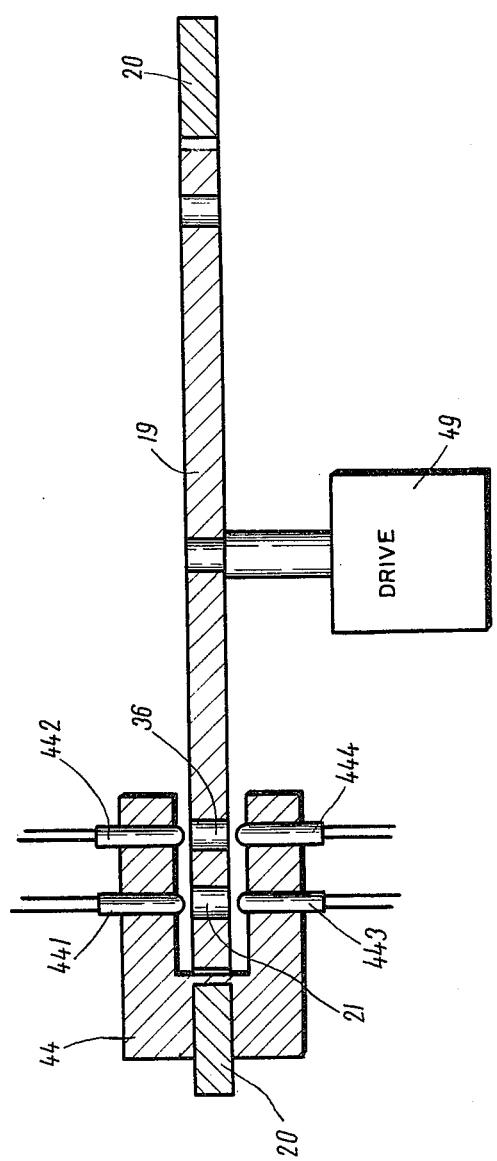
FIG. 3 is a partially sectional view of a source of pseudorandom sequences of orders.

FIG. 3 is a partial sectional view of the generator 18; as shown in FIG. 2, where the arrangement of the rotor 19, the driving device 49, the stator 20 and of the photoelectric indicator 44 is visible, which latter is composed of a couple of emission diodes 441, 442, and phototransistors 443, 444.

The method and operation of the arrangement according to this invention can be explained for instance by example of a quick continuous pressure liquid chromatography as shown in FIG. 1. The elution liquid is pumped from the storage tank 1 of the elution liquid by the pump 2 into a degaser 3 and thereafter to the shock absorber 4. The elution liquid thus free of gases and stabilized passes thereafter through the dosing device 5 into the separating device 6 i.e. into a separating chromatographic column. The sample to be analyzed, i.e. specifically a mixture of components $L_1$, $L_2$, $L_3$, (FIG. 4) which have to be followed and of components $L_4$... $L_n$, which need not be followed is supplied by the dosing device 5 to the throughflowing elution liquid at pseudorandom sequences, determined by the generator 18. In the course of passage of the mixture of the sample the components are separated in a known manner as they proceed through the column 6 at different speed. The signal of the concentration detector 7 of contains therefore the information about the relative content of individual components in the sample. The signal after amplification by the amplifier 8 is passed to the analog-digital converter 12 and recorded both by the analog recorder 9 and by the multichannel digital recorder 10. The digital signal is in a suitable order, preferably corresponding to the pseudorandom sequence supplied via the gates 141, 142, 143, 144, 145 to counters 151, 152, 153, 154, 155. The suitable order is determined by the generator 18 and is obtained by opening and closing of gates 141, 142, 143, 144, 145. The counters 151, 152, 153, 154, 155 count the digital signal passed by the gates 141, 142, 143, 144, 145 for the time determined by the generator 18.

The signals of the photoelectric indicators 44, 45, 46, 47 and 48 control the process of dosing by the dosing device and the evaluation process by the counters 151, 152, 153, 154, 155. The position of the photoelectric indicators 44, 45, 46, 47, 48 on the stator 20 and their number determine which components and how many components (in the given case three components $L_1$, $L_2$, $L_3$) will be followed by concentration. The relative position of the photoelectric indicators 44, 45, 46, 47, 48 on the stator 20 is determined by the relative speeds at which the individual components of the sample pass through the chromatographic column 6.

Figure 4:
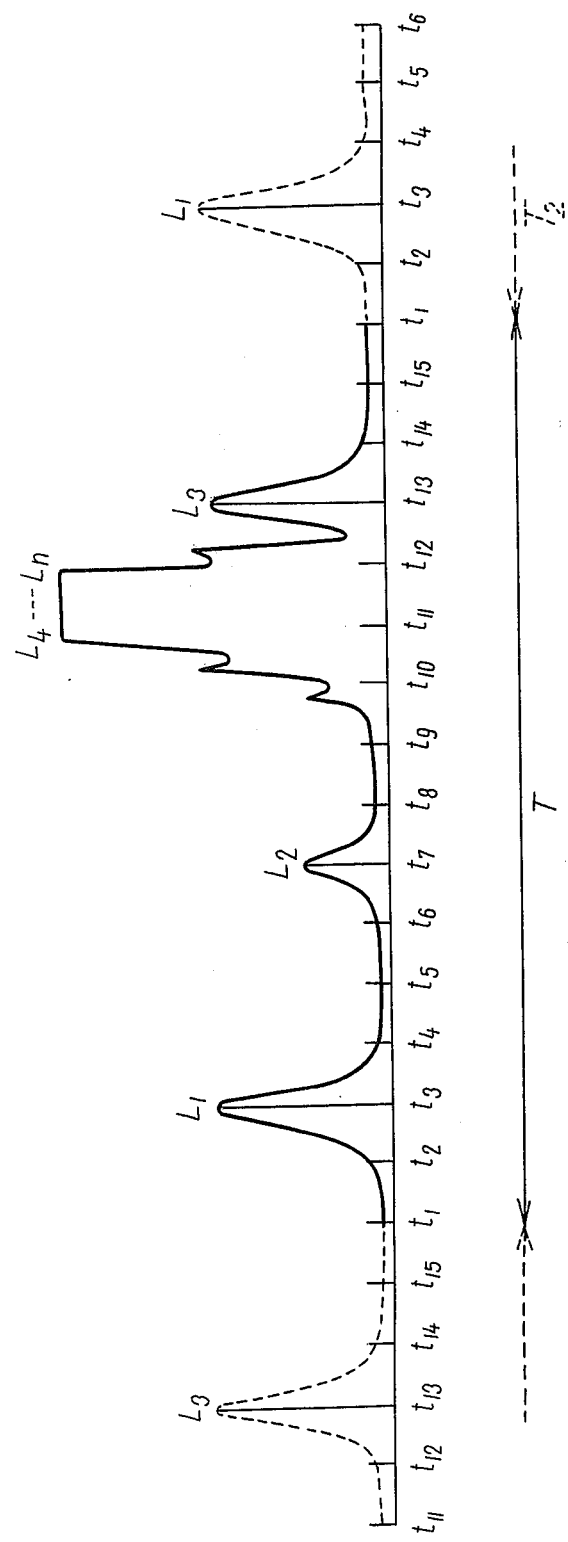
FIG. 4 is an explicite comparison of the old chromatographic method with the method according to this invention with an example of a graphical representation of results of the analysis carried out with both methods.

FIG. 4 is used for showing the course of the separating process, in the case given a liquid chromatographic process in dependence on time, according to the old method is compared simultaneously the time course of the separating process according to the new method. At the moment $t_1$ the sample comprising n components, from which $L_{1, 2, 3}$ are important and sensed, $L_{4, 5 \ldots n}$ are not sensed and not significant is introduced into the elution liquid at the inlet into the chromatographic column 6 (FIG. 1). The components $L_{i = 1 \text{ to } n}$ subsequently proceed through the column 6 at different speed. The concentration detector 7 at the outlet from the column 6 converts variations of concentration to variations of the electric signal, which is registered after amplification. It is apparent from FIG. 4 that the the components of the sample reach the detector 7 in a sequence $L_1 - L_2 - L_{4 \text{ to } n} - L_3$, whereby the component $L_1$ is at the moment $t_3$, the component $L_2$ is at the moment $t_7$ and the component $L_3$ is at the moment $t_{13}$. Components which are not significant are indicated by the detector 7 within the time interval $t_{9 \text{ to } 12}$. The whole process can be considered to be completely finished when all components of the sample have left the column 6 i.e. at the moment $t_{15}$; the whole time of duration of the process i.e. the period is called T and is in this example fifteen times longer than a time interval $t_n - t_{n-1}$. A further sample for repeating the process can be introduced to the inlet of the column 6 only after lapse of this time T.

According to the new method the sample is not introduced only at the moment $t_1$, but many times in the course of the whole period T and possibly also in the course of further periods $T_{2, 3} \ldots$ a.s.f. Through the detector 7 (FIG. 1) at the outlet of the column 6 flows therefore not one component after the other, but a mixture of a number of components and the signal of the detector 7 represents a superposition of signls corresponding to these samples. It is thus obvious from this description, that for the same response of the detector 7, i.e. for an average value of the signal, a lower concentration of the individual sample will be required, than at the old method, the absolute amount will be of course equal for both methods.

In the example the pseudorandom sequence is derived from a four bit fundamental sequence 0001 and comprises the following 15 (i.e. $2^4 - 1$) elements. 100010011010111, i.e. eight ones and seven zeros. The place of the earlier mentioned pseudorandom sequences is a one, the same as on the first place, the number one represents an order for sampling, a zero for not sampling. The signal of the detector 7 will at the moment $t_8$ correspond to components 8, 4 and 1 from the first, second and third sampling. Similarly at the last moment of period T, i.e. at the time $t_{15}$ the signal of the detector 7 will correspond to components 15, 11, 8, 7, 5, 3, 2, 1 from the first up to eight sampling. In case of a single analysis, the sampling can now be finished and the components will subsequently leave the column in the course of the following period $T_2$, so that at the moment $t_{15}$ of this period $T_2$ no more component will be in the column. In case of a continuous analysis however the sampling is continued also in the course of periods $T_{2, 3} \ldots$ If the composition of the sample to be analyzed does not change, the response of the detector 7 i.e. its signal will be at the time $t_1$ proportional to the content of components 1 12 9 8 6 4 3 2 at the time $t_2$ proportional to the content of components 2 13 10 9 7 5 4 3 at the time $t_3$ proportional to the content of components 3 14 11 10 8 6 5 4 and so forth.

at the time $t_{14}$ proportional to the content of components 14 10 7 6 4 2 1 15 at the time $t_{15}$ proportional to the content of components 15 11 8 7 5 3 2 1

In case of a single analysis quite equal values are obtained by addition of signals $t_1$ to $t_{15}$ from the first and second period ($T + T_2$).

If the output of the detector 7 is recorded by a suitable recording device (for instance by an analog recorder 9) an operation without faults of the followed chemical (or other) process can be ascertained by comparison of the record with the standard record.

If however digital records are required, it is possible by using the pseudorandom sequence in the same manner as has been used for the control of dosing to work the sequence of informations of the detector 7 as follows:

| pseudorandom sequence | information for the time $t_i$ | component |||||||||||||||
|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| 1 | 1 | + | + | + | + |   | + |   | + | + |   | + |   |   |   |   |
| 0 | 2 |   | + | + | + | + |   | + |   | + | + |   | + |   | + |   |
| 0 | 3 |   |   | + | + | + | + |   | + |   | + | + |   | + |   | + |
| 0 | 4 | + |   |   | + | + | + | + |   | + |   | + | + |   | + |   |
| 1 | 5 | + |   |   |   | + | + | + | + |   | + |   | + | + |   |   |
| 0 | 6 |   | + |   |   |   | + | + | + | + |   | + |   | + | + |   |
| 0 | 7 |   |   | + |   |   |   | + | + | + | + |   | + |   | + | + |
| 1 | 8 | + |   |   | + |   |   |   | + | + | + | + |   | + |   | + |
| 1 | 9 | + | + |   |   | + |   |   |   | + | + | + | + |   | + |   |
| 0 | 10 |   | + | + |   |   | + |   |   |   | + | + | + | + |   | + |
| 1 | 11 | + |   | + | + |   |   | + |   |   |   | + | + | + | + |   |
| 0 | 12 |   | + |   | + | + |   |   | + |   |   |   | + | + | + | + |
| 1 | 13 | + |   | + |   | + | + |   |   | + |   |   |   | + | + | + |
| 1 | 14 | + | + |   | + |   | + | + |   |   | + |   |   |   | + | + |
| 1 | 15 | + | + | + |   | + |   | + | + |   |   | + |   |   |   | + |
| Sums | | $S_1$ | $S_2$ | $S_3$ | $S_4$ | $S_5$ | $S_6$ | $S_7$ | $S_8$ | $S_9$ | $S_{10}$ | $S_{11}$ | $S_{12}$ | $S_{13}$ | $S_{14}$ | $S_{15}$ | signal of the detector 7 will therefore correspond at the time $t_1$ (FIG. 4) of the period T i.e. at the moment of the first sampling to a hypothetical sample with infinite speed, i.e. corresponding to no component and thus to the sole elution liquid with a zero concentration of admixtures, at the moment $t_2$ to component 2, at the moment $t_3$ to component 3. At the moemnt $t_5$ component 1 will show in addition to component 5, as at this moment the second sampling takes place. At the fifth If we mark the sum of all concentrations of all components $C_o$ and the concentration of individual components $C_1$ to $C_{15}$, than $$C_o = C_2 \ldots + C_{14} + C_{15}.$$

The reference summation (the sum) will thereafter be according to the above summarizing schedule. $S_1 =$ record for the time $t_1$ + record for the time $t_5$ + record for the time $t_{8, 9, 11, 13, 14}$ + record for the time $t_{15}$.

It can be proved that this reference summation will be equal to four times $(C_o + C_1)$. Analogically the summation of the second column marked as component 2 will be equal to $4(C_o + C_2)$, the summation of the third column $4(C_o + C_3)$ a.s.f. As $C_1$ is apriori equal to zero, the result of the first sammation is the sum of all concentrations of all components of the sample and substitute therefore the internal standard and the results of all remaining summations can be referred to this value.

In the example referred to the first summation will be realized as the reference standard summation, the third, sevents and thirteenth summation as corresponding to following components $L_1$, $L_2$, $L_3$.

The concentration of component $L_1$ in percentage of the content the sample will be thereafter:

$$C_{L_1} = 100 \cdot \frac{S_3 - S_1}{S_1} \text{ analogically}$$

$$C_{L_2} = 100 \cdot \frac{S_7 - S_1}{S_1} \text{ and finally}$$

$$C_{L_3} = 100 \cdot \frac{S_{13} - S_1}{S_1}$$

FIG. 4 shows the resulting concentrations symbolically by line segments $L_{1, 2, 3}$. As however at the process according to this invention the dosing proceeds not only in the course of one, but in the course of more periods, the informations about the content of components in the samples are equally obtained in the course of more periods. Some occasional disturbance, for instance some noise showed on the detector 7 in earlier used methods concentrated at the just followed component. According to the new method according to this invention this disturbance affects the followed component in a limited degree only, in the example only with one eighth of its magnitude and affects also the results of the other summations including the reference summation so that the disturbance is to a high degree compensated. If we exchange mutually the zeros and ones for the random sequence, it is possible to obtain at an analogical process of dosing and evaluating equally correct results, the formulas are only slightly different namely.

$$S_1^{inverse} = 4C_1 + 3C_o, \quad S_2^{inverse} = 4C_2 + 3C_o \text{ a.s.f.}$$

The common rule is that if the period T is divided to $(2^n - 1)$ parts, the correct pseudorandom sequence will contain $(2^{n-1} - 1)$ zeros, $2^{n-1}$ ones, in one summation there will be $(2^{n-2})$ informations about a respective component and the same number of informations about all components of the sample. By selection of n it is possible to change the fineness of the chromatographic separation up to the limit of separating properties of the column 6, to change the sensitivity and to change the degree of improvement of the ratio signal to noise. When there is no need for an internal standard for analysis than a bidirectional counter may be used. In this case ones represent plus orders (subtraction orders). In practical example we have e.g. $S_3 = 8 \times L_1$, $S_7 = 8 \times L_2$ and $S_3 = 8 \times L_3$.

I claim:

1. A method for performing a separating analysis, wherein the sample to be analyzed is dosed into a separating device and a signal generated in response thereto, corresponding to the concentration of individual components of the sample at the outlet of the separating device within certain time intervals, comprising the steps of dosing the sample in a regular rhytmus at equal doses in pseudorandom sequences according to a program for dosing comprising a recorded set of binary instructions, containing a given number of $x = 2^n - 1$ orders, where n is an integer positive number and the orders are of a binary character, the time of duration of one pseudorandom sequence being determined by the rhytmus and mumber of orders being chosen at least equal to the time of duration of the passage of the slowest component through the separating device, the instantaneous values of the output signal, proportional to the instantaneous summary concentrations of components of the sample being read by a detector in a rhytmus proportional to the rhytmus of dosing orders, the separating analysis being thereafter carried out based on summation of the read values by a control program comprising a recorded set of binary instructions derived from the program for dosing the sample.

2. The method according to claim 1 wherein the amount of the sample of one dose is chosen proportional to the sensitivity of the detector in the range of its linear response.

3. The method according to claim 1, wherein the number x of said orders is chosen according to the required fineness of separation.

4. The method according to claim 1, wherein the number of summations is equal at least to the sum of chosen components of the sample and to the chosen number of reference summations and at the most to the number of orders of one pseudorandom sequence, the result of the first summation being chosen as a main reference summation used as an internal standard of the separating analysis.

5. The method according to claim 1, wherein the result of the last summation is chosen as an auxiliary reference summation in order to check the finished separating process.

6. The method according to claim 1 where when evaluating the separating analysis, the values of the output signal of the detector, proportional to the sum of instantaneous concentrations of components of the sample, read in a rhytmus proportional to the rhytmus of dosing orders, are added at the first summation according to the instantaneous binary state of the fundamental pseudorandom sequence $x$, whereby for the second, third, fourth to $x^{th}$ summation they are added according to the instantaneous binary state of the pseudorandom sequence drived from the fundamental sequence, contained in the program for dosing by cyclical shift by one, two, three to $(x-1)$ positions.

7. The method according to claim 1, the concentration of the second to $x^{th}$ component of the sample being derived from results of the second to $x^{th}$ summation.

8. Apparatus for performing a separation analysis, comprising a separating column, a dosing device for dosing the sample to be analyzed connected to its inlet, a generator of pseudorandom sequences of orders for the dosing device, a detector connected to the output of the separating column, an amplifier, an analog-digital converter, a number of gates and counters, the control inlet of the dosing device connected with the first output of the generator of pseudorandom sequences of order, the output of the detector connected to the input of the amplifier, the output of which is connected with the input of the analog-digital converter, the output of which is connected with inputs of electronic gates, the control inputs of which are connected with second outputs of the generator of pseudorandom sequences of orders, the outputs of the gates connected with inputs of counters.

9. The apparatus according to claim 8, wherein the input of an analog recording device is connected to the output of the amplifier.

10. The apparatus according to claim 8, including a multichannel digital recording device connected to the output of the analog-digital converter and to the outputs of the generator of pseudorandom sequences.

11. The apparatus according to claim 8, wherein the source of pseudorandom sequences comprises a rotor of light impervious material provided with openings and a stator provided with photoelectric indicators of said openings in the rotor, whereby the photoelectric indicators are mutually relatively shiftable.

* * * * *